United States Patent [19]

Hunsucker

[11] 4,092,144
[45] May 30, 1978

[54] METHOD OF CONTROLLING THE GROWTH OF ALGAE AND VIRUSES USING MEMBERS OF THE CLASS OF OXAZOLIDINES

[75] Inventor: Jerry Hoyt Hunsucker, Terre Haute, Ind.

[73] Assignee: IMC Chemical Group, Inc., Terre Haute, Ind.

[21] Appl. No.: 748,429

[22] Filed: Dec. 8, 1976

Related U.S. Application Data

[60] Continuation-in-part of Ser. No. 588,744 Jun. 20, 1975, which is a division of Ser. No. 469,200, May 13, 1974.

[51] Int. Cl.² ............................ A01N 9/22; A01N 9/28
[52] U.S. Cl. .................................. 71/67; 260/307 FA; 424/272
[58] Field of Search .......................... 424/272; 71/67; 260/307 FA

[56] References Cited

U.S. PATENT DOCUMENTS

| | | | |
|---|---|---|---|
| 2,250,408 | 7/1941 | Groote | 260/307 FA X |
| 2,448,890 | 9/1948 | Johnston | 260/307 |
| 3,160,634 | 12/1964 | Hodge | 260/307 X |
| 3,256,137 | 6/1966 | Danielson | 260/307 FA X |
| 3,257,320 | 6/1966 | Hodge | 252/51.5 |
| 3,266,970 | 8/1966 | Paul | 161/241 |
| 3,281,311 | 10/1966 | Paul | 161/241 |
| 3,707,541 | 12/1972 | Lajiness | 260/244 R |
| 3,738,992 | 6/1973 | Frump | 260/307 F |
| 3,824,309 | 7/1974 | Schnegelberger | 424/272 |

FOREIGN PATENT DOCUMENTS

1,903,864  8/1970  Germany.

OTHER PUBLICATIONS

Senkus, J. Am. Chem. Soc. 67, 1515–1519 (1945).
Danielson, Chem. Abst. vol. 58 (1963) 12750b.

*Primary Examiner*—Allen J. Robinson
*Attorney, Agent, or Firm*—Robert H. Dewey; Howard E. Post

[57] ABSTRACT

The disclosed oxazolidines are useful as anti-algal and anti-viral agents. The compounds are of a low order of toxicity to warm-blooded animals.

4 Claims, No Drawings

METHOD OF CONTROLLING THE GROWTH OF ALGAE AND VIRUSES USING MEMBERS OF THE CLASS OF OXAZOLIDINES

CROSS-REFERENCE TO RELATED APPLICATIONS

This is a continuation-in-part of copending application Ser. No. 588,744 filed June 20, 1975 which is a division of copending application Ser. No. 469,200 filed May 13, 1974.

BACKGROUND OF THE INVENTION

This invention relates to a method of controlling the growth of algae and viruses. In a particular aspect this invention relates to a method of controlling the growth of algae and viruses by applying thereto certain members of the class of oxazolidines.

Oxazolidines have long been known in the art. They are readily prepared by reacting an amino alcohol with an aldehyde:

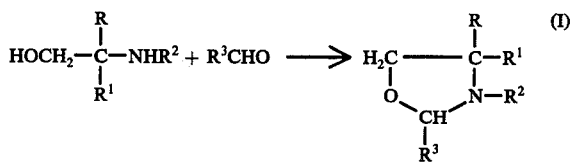

If the amino alcohol is a diol and 2 moles of aldehyde are used, the resulting oxazolidine is bicyclic, as described by M. Senkus, J. Am. Chem. Soc. 67, 1515-1519 (1945) and Wm. B. Johnston, U.S. Pat. No. 2,448,890.

It is an object of this invention to provide a method of controlling the growth of microorganisms including viruses.

It is another object of this invention to control the growth of algae and viruses by applying thereto certain members of the class of oxazolidines.

It is yet another object of this invention to provide novel oxazolidines.

Other objects of this invention will be apparent to those skilled in the art from the disclosure herein.

It has been discovered that the growth of algae and viruses is controlled by applying to these organisms an oxazolidine corresponding to formula I wherein R and $R^1$ can be hydrogen or alkyl of 1 or 2 carbons and can be the same or different; $R^2$ can be hydrogen or alkyl of from 1 to 3 carbon atoms; $R^3$ is hydrogen or alkyl of from 1 to 3 carbon atoms.

DETAILED DESCRIPTION

Some of the oxazolidines used in the practice of this invention are commercially available and the usual commercial materials are suitable. 4,4-Dimethyl-1,3-oxazolidine is generally known as Oxazolidine A and this designation is employed in the examples. Other oxazolidines, made from aldehydes other than formaldehyde, can be made by the method of M. Senkus or Wm. B. Johnston or J. A. Frump, U.S. Pat. No. 3,738,992.

Most of these oxazolidines are water-soluble and are conveniently applied to the environment inhabited by microorganism as a water solution. They are particularly effective in aqueous systems such as starch adhesives and solutions, drilling muds for the petroleum industry and in water-dilutable cutting oils based on petroleum hydrocarbons. A concentration of about 10–1000 µg/ml is required, but generally about 100–500 µg/ml is sufficient for all but the heaviest infestations.

These oxazolidines are also soluble in, e.g., alcohols, ketones and most other organic solvents, including hydrocarbons. Solutions of the water-insoluble oxazolidines in such solvents can be used in substantially non-aqueous or 2-phase systems when desired.

The invention will be better understood by reference to the following examples. It is understood, however, that the examples are intended only for the purpose of illustration and it is not intended that the invention be limited thereby.

EXAMPLE 1

Oxazolidine A (4,4-dimethyl-1,3-oxazolidine) was tested for anti-algal and anti-viral activity by known methods. The results were reported as the minimum inhibitory concentration (MIC) required to inhibit growth. The MIC is actually the range between the highest concentration that permits growth and the lowest concentration that inhibits growth. The results obtained are as follows:

|  | MINIMUM INHIBITORY CONCENTRATION |
|---|---|
| ALGAE | |
| Six species of green and blue-green | 19.5–156 µg/ml |
| VIRUS | |
| Newcastle's strain | 100–1000 µg/ml |
| Boney-1 strain | 100–1000 |

Oxazolidine A is added to recirculating water in an ornamental fountain at a concentration of about 200–500 µg/ml to prevent the growth therein of algae and brown slime organisms.

Oxazolidine A is used as a disinfectant for utensils used in food service to prevent the growth and spread of viruses causing colds and influenza. The utensils are soaked briefly in water containing Oxazolidine A at a concentration in the range of 1 mg/ml (1000 µg/ml) to 100 mg/ml.

EXAMPLE 2

The object of the following experiment was to determine the concentration of Oxazolidine A required to prevent attack by soil organisms on a starch-based drilling mud.

A starch solution, simulating a starch-based drilling mud, was prepared by dispersing 100 g of starch in 150 g of deionized water, then diluting with 2000 g of deionized water. Aliquots of 200 g each of this solution were then delivered to 4 oz jars.

A suspension of soil organisms was prepared by extracting 5 g of ordinary soil with 100 ml of water. To the starch solution in each of the 4 oz jars was added 1 ml of the suspension of soil microorganisms. The pH was adjusted to 7 and to each of 3 jars there was added sufficient Oxazolidine A to provide a concentration of 0.1%, 0.2% and 0.3%, respectively. The jars were then incubated at 37° C for 96 hours.

After the incubation period, sterile agar plates were inoculated with supernatant liquid from the jars. The plates were then incubated for another 24 hours and results were recorded as growth or no growth. None of the samples treated with Oxazolidine A showed any growth. A control sample without oxazolidine showed growth.

EXAMPLE 3

The experiment of Example 2 was repeated in all essential details except that one group of samples was adjusted to pH 5 and another to pH 9. No growth was observed in those treated with Oxazolidine A but growth did occur in the controls without oxazolidine.

EXAMPLE 4

The experiment of Example 1 is repeated in all essential details except that 1,3-oxazolidine is substituted for 4,4-dimethyl-1,3-oxazolidine (Oxazolidine A). Inhibition of algae and the virus strains is obtained at concentrations of 10–1000 μg/ml.

EXAMPLES 5 – 8

The experiment of Example 1 is repeated in all essential details except that another oxazolidine was substituted for Oxazolidine A in equi-molar amounts. The oxazolidines used had the following substituents:

| Example | R | $R^1$ | $R^2$ | $R^3$ |
|---|---|---|---|---|
| 5 | hydrogen | ethyl | hydrogen | hydrogen |
| 6 | methyl | methyl | methyl | methyl |
| 7 | methyl | methyl | hydrogen | propyl |
| 8 | methyl | methyl | methyl | ethyl |

I claim:

1. A method of combatting the growth of algae and New Castle's virus and Boney virus by applying thereto a growth-inhibiting amounts of an oxazolidine represented by the formula:

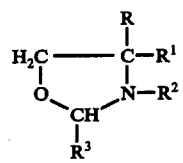

wherein R and $R^1$ are hydrogen or alkyl of 1 to 2 carbon atoms and can be the same or different; $R^2$ is hydrogen or alkyl of 1 to 3 carbon atoms; $R^3$ is hydrogen or alkyl of from 1 to 3 carbon atoms.

2. The method of claim 1 wherein said oxazolidine is 4,4-dimethyl-1,3-oxazolidine.

3. The method of claim 1 wherein said growth-inhibiting amounts are in the range of from 10 μg/ml to 1000 μg/ml.

4. The method of claim 1 wherein $R^3$ is methyl.